(12) United States Patent
Karembe et al.

(10) Patent No.: US 9,877,969 B2
(45) Date of Patent: *Jan. 30, 2018

(54) TREATMENTS WITH TRIAZINES

(71) Applicant: CEVA SANTE ANIMALE, Libourne (FR)

(72) Inventors: Hamadi Karembe, Libourne (FR); Roman Krejci, Libourne (FR); Jérôme Guyonnet, Ambares (FR); Hannelie Cilliers, Gauteng (ZA)

(73) Assignee: CEVA SANTE ANIMALE, Libourne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/650,046

(22) PCT Filed: Dec. 6, 2013

(86) PCT No.: PCT/EP2013/075755
§ 371 (c)(1),
(2) Date: Jun. 5, 2015

(87) PCT Pub. No.: WO2014/086958
PCT Pub. Date: Jun. 12, 2014

(65) Prior Publication Data
US 2015/0313905 A1 Nov. 5, 2015

(30) Foreign Application Priority Data
Dec. 7, 2012 (EP) ..................... 12306546

(51) Int. Cl.
*A61K 31/53* (2006.01)
*A61K 31/7135* (2006.01)
*A61K 9/00* (2006.01)
*A61K 33/26* (2006.01)
*A61K 45/06* (2006.01)

(52) U.S. Cl.
CPC ............ *A61K 31/53* (2013.01); *A61K 9/0019* (2013.01); *A61K 31/7135* (2013.01); *A61K 33/26* (2013.01); *A61K 45/06* (2013.01)

(58) Field of Classification Search
CPC ... A61K 31/53; A61K 9/0019; A61K 31/7135
USPC .................................................. 514/25, 241
See application file for complete search history.

(56) References Cited

U.S. PATENT DOCUMENTS

| 4,493,826 A * | 1/1985 | Strayer .................. A61K 31/70 424/118 |
| 6,465,460 B1 | 10/2002 | Hundley et al. |
| 7,915,257 B2 | 3/2011 | Greif et al. |
| 2015/0320756 A1 | 11/2015 | Karembe et al. |

FOREIGN PATENT DOCUMENTS

| CA | 2688613 | 12/2008 |
| DE | 10 2007 02590 | 12/2008 |
| WO | WO 02/14288 | 2/2002 |
| WO | WO 2010/146155 | 12/2010 |
| WO | WO 2014/086959 | 6/2014 |
| WO | WO 2014/086960 | 6/2014 |

OTHER PUBLICATIONS

Glossary of medical education terms, Institute of International Medical Education. http://www.iime.org/glossary.htm Accessed in Mar. 2013.*
Mundt et al. Efficacy of Toltrazuril against Artificial Infections with Eimeria bovis in Calves. Parasitol Res (2003) 90: S166-S167.*
Mundt. Baycox® 5 %: An Anticoccidial for the Treatment of Isospora Suis Coccidiosis in Piglets. 16 th Congress of the International Pig Veterinary Society Sep. 17-21, 2000.*
Pan, B.L., et al., "Effect of subcutaneously administered diclazuril on the output of *Eimeria* species oocysts by experimentally infected rabbits," *The Veterinary Record*, Feb. 2, 2008, vol. 162, No. 5, pp. 153-155.
Friend, M. et al. "Intestinal Coccidiosis" *Field Manual of Wildlife Diseases: General Field Procedures and Diseases of Birds*, 1999, pp. 207-214, Section 5, Cpt. 26.
Halls, A. "Coccidiosis in Rabbits" *Nutrifax Nutrition News and Information Update*, Nov. 2005, pp. 1-7.
"Veterinary Medicinal Product Evaluation Report; Drug containing Toltrazuril as an active ingredient and administered to cattle and pigs by gavage (Baycox for cattle, Baycox for pigs)" Food Safety Commission, Veterinary Medicinal Product Expert Committee, Apr. 2008, pp. 1-9.
Saito, Y. "Coccidia *Isospora suis* in Pig (to obtain piglets having uniform weight at weaning)" date unknown, pp. 1-5. (2005).

* cited by examiner

*Primary Examiner* — Yih-Horng Shiao
(74) *Attorney, Agent, or Firm* — Saliwanchik, Lloyd & Eisenschenk

(57) ABSTRACT

The invention relates to improved methods for protecting non-human animals with triazine compounds by intramuscular or subcutaneous injection(s). The invention can be used with various triazines, such as toltrazuril, in different non-human animals, such as a porcine, an ovine, a bovine, a canine, a feline, or an avian, for protecting them against infectious diseases, such as protozoan disorders.

17 Claims, 4 Drawing Sheets

(A)

(B)

(C)

TREATMENTS WITH TRIAZINES

CROSS-REFERENCE TO RELATED APPLICATION

Figure 1:
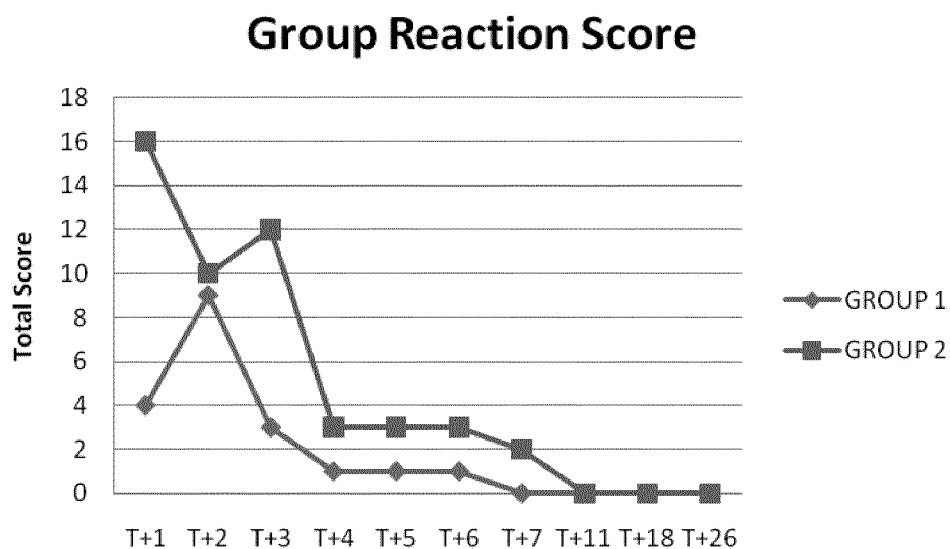

This application is the U.S. national stage application of International Patent Application No. PCT/EP2013/075755, filed Dec. 6, 2013.

The present invention relates to novel triazine-based treatments of non-human animals. The invention also relates to improved methods for the preventive treatment of non-human animals with triazine compounds by intramuscular or subcutaneous injection(s). The invention can be used with various triazines, such as clazuril, diclazuril, letrazuril, sulazuril, toltrazuril, and their active metabolites such as toltrazuril sulfoxide and toltrazuril sulfone (e.g., ponazuril), in different non-human animals such as a porcine, an ovine, a bovine, a canine, a feline or an avian, for protection against infectious diseases, such as protozoal disorders.

INTRODUCTION

Triazines are commonly used in the veterinary industry to treat non-human animals against a variety of diseases. Triazines are broad-spectrum antimicrobials that inhibit both gram-positive and gram-negative bacteria, as well as some protozoa, such as coccidia. Triazines, such as toltrazuril and ponazuril, are authorized agents for protecting against coccidioses, which are frequent parasitic infectious diseases caused by protozoans, e.g., *Eimeria* or *Isospora*. Triazines are also effective against other protozoal parasites, e.g., *Toxoplasma*, cryptosporidia, or *sarcocystis*.

Triazines are essentially administered to the non-human animals by an oral route.

In this regard, EP116175 refers to a water miscible solution of a triazine for oral administration. DE19603954 proposes triazine granules for oral administration and DE19824483 relates to semi-solid preparations which are applied orally.

EP2164496 relates to triazine-iron combination products. The triazine compound is administered orally, as a suspension.

Oral administration, however, presents drawbacks. Indeed, oral administration prevents strict control of the dosage administered to each non-human animal. Also, oral administration cannot be combined with other treatments which are given by injection (e.g., antibiotics, anti-inflammatory agents, anthelmintics, endectocides, minerals or vitamins) and therefore involves additional manipulation of the non-human animals.

Administration of triazines by transdermal application has been proposed in US2010/0179151. Transdermal application as proposed in US2010/0179151 comprises a spot-on formulation which is applied on the skin and taken up by passive percutaneous absorption. Again, such administration route does not allow a strict control of the dosage administered to each non-human animal. Also, transdermal administration cannot be combined with other treatments which are given by injection (e.g., antibiotics, anti-inflammatory agents, anthelmintics, endectocides, minerals such as iron, or vitamins).

WO01/26660 and U.S. Pat. No. 6,465,460 relate to a sodium salt of triazine compounds and to compositions for oral or parenteral administration. According to this patent the sodium salt allows the use of lower doses of the compound. Although different administration routes are mentioned, all of the experimental section is limited to intravenous and oral administration. Furthermore, the patent indicates that several administrations and/or a sustained release dose are required for maintaining appropriate blood levels. In particular, the patent proposes a starting dose and several maintenance doses, which need to be administered over several days.

Despite preliminary investigations of different routes (e.g., transdermal), oral administration is still preferred today because it is believed to provide the most appropriate pharmacokinetic profile of the drug, especially in young non-human animals. In particular, while the oral formulation requires substantive manipulation and cannot provide a strict dosage control, it is believed to ensure appropriate bioavailability and therapeutic efficacy of the triazine compounds.

It has now been found that triazines may be administered by intramuscular or subcutaneous injection. Surprisingly, the inventors have found that full activity can be achieved with a single intramuscular injection of triazines, and that such administration provides and maintains the required effective plasma levels in the active agent to protect the non-human animal against infectious diseases, particularly caused by protozoans such as coccidia. In the specific case of toltrazuril, although the intramuscular application modifies the pharmacokinetic profile of toltrazuril itself, it has now been surprisingly found that such application leads to an optimized pharmacokinetic profile of the active metabolite thereof, toltrazuril sulfone. The invention thus allows an efficient administration of triazines, even at very early stages of growth of the non-human animals, and may be further combined with other agents that are administered by injection such as antibiotics, anti-inflammatory agents, anthelmintics, endectocides, minerals or vitamins

SUMMARY OF THE INVENTION

An object of the invention resides in a composition comprising a triazine for use in the preventive treatment of a non-human animal, wherein said composition is administered by intramuscular or subcutaneous injection.

Another object of the invention resides in a composition comprising a triazine for use to protect a non-human animal against an infectious disease, wherein said composition is administered by intramuscular or subcutaneous injection.

Another object of the invention resides in a method for the preventive treatment or for the protection of a non-human animal against an infectious disease, the method comprising the intramuscular or subcutaneous injection to said non-human animal of a composition comprising an effective amount of a triazine.

Another object of the invention resides in a method for administering a triazine to a non-human animal, the method comprising the intramuscular or subcutaneous injection of a composition comprising said triazine to said non-human animal.

The compositions of the invention are more preferably administered by a single injection to the non-human animal.

Preferred embodiments of the invention involve the use of one of the following triazines:

Derivatives of 1,2,4-triazinedione, such as clazuril, diclazuril, letrazuril and sulazuril; or Derivatives of 1,3,5-triazinetrione, such as toltrazuril, toltrazuril sulfoxide, and toltrazuril sulfone (e.g., ponazuril).

The composition may comprise further active agents, such as antibiotics, anthelmintics, endectocides, anti-inflammatory agents and/or vitamins, and/or minerals, for single, grouped, separated or sequential intramuscular or subcutaneous injection.

Preferably, the triazine and the other agents are combined in the same formulation for a single intramuscular or subcutaneous injection.

The invention may be used for the preventive treatment of any infectious disease in said non-human animal, preferably a protozoan disease, more preferably of the blood (such as babesiosis, sarcocystosis, or toxoplasmosis), or of the digestive tract (such as coccidiosis).

The invention is particularly suited for protecting a porcine, an ovine, a bovine, a canine, a feline or an avian against infectious diseases. It may be used in adults or young non-human animals, such as newborn to 10-day-old non-human animals.

LEGEND TO THE FIGURES

FIG. 1: Reaction Score of treated and non-treated piglets: G1: Intramuscular 20 mg/kg by body weight (0.4 ml/kg); G2: Intramuscular 40 mg/kg by body weight (1.2 ml/kg).

Figure 2:
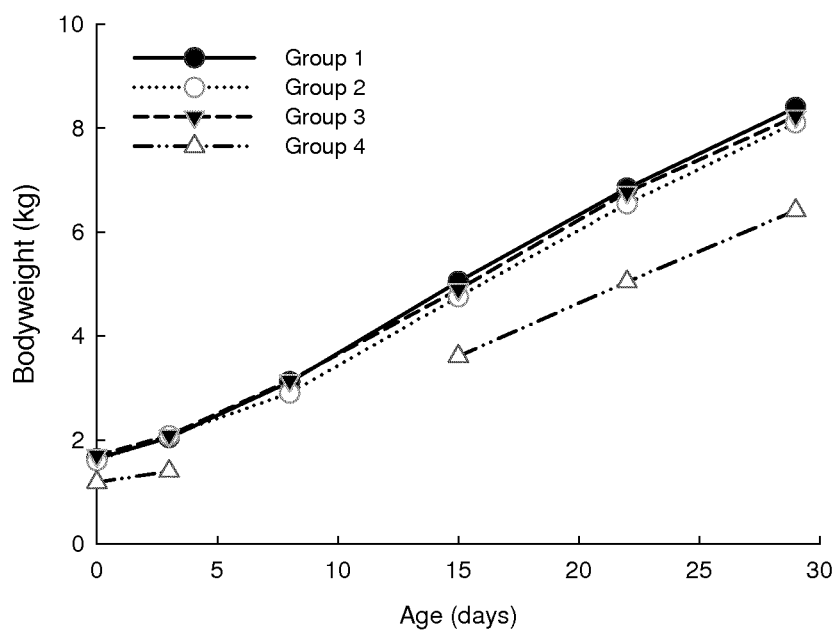

FIG. 2: Average weight gain of treated and non-treated piglets: G1: Intramuscular 20 mg/kg by body weight (0.4 ml/kg); G2: Intramuscular 40 mg/kg by body weight (1.2 ml/kg); G3: Oral 20 mg/kg by body weight (0.4 ml/kg); G4: Control, not treated.

Figure 3:
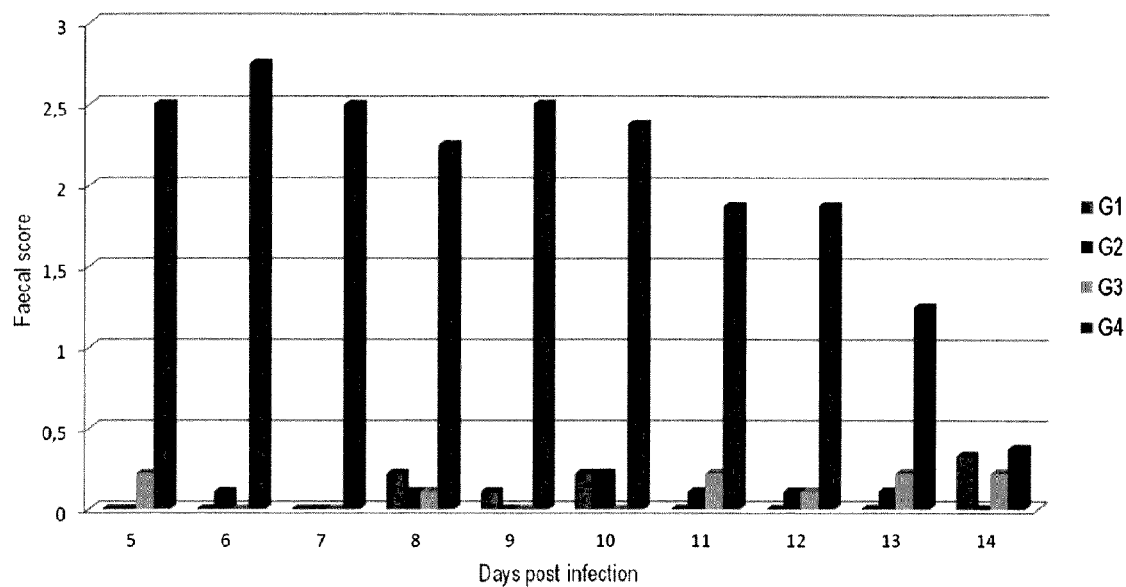

FIG. 3: Fecal consistency of treated and non-treated piglets.

Figure 4:
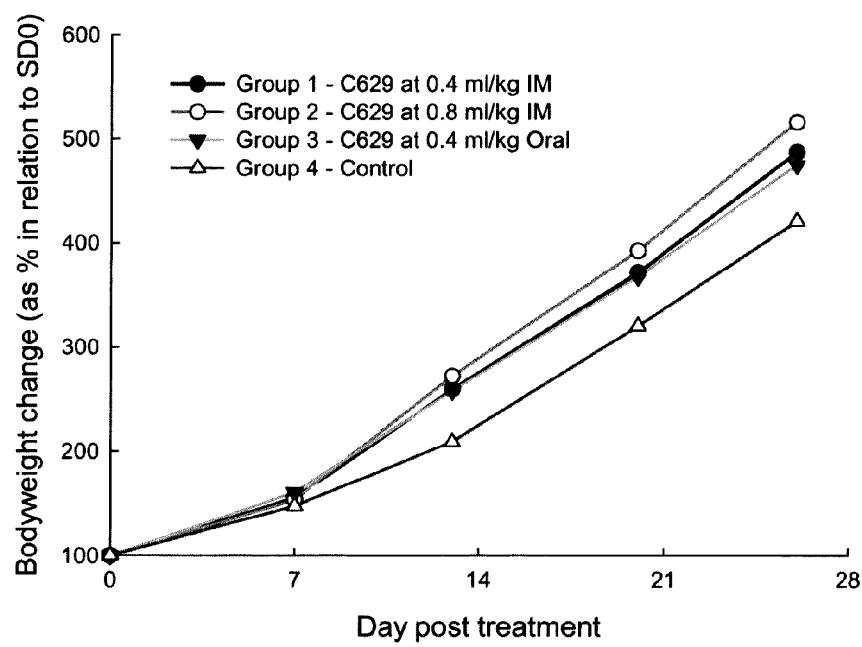

FIG. 4: Body weight change of treated and non-treated piglets following intramuscular injection of 20 mg/kg by body weight (Group 1); intramuscular injection of 40 mg/kg by body weight (Group 2); oral administration of 20 mg/kg by body weight (Group 3) or non-treated control (Group 4).

Figure 5:
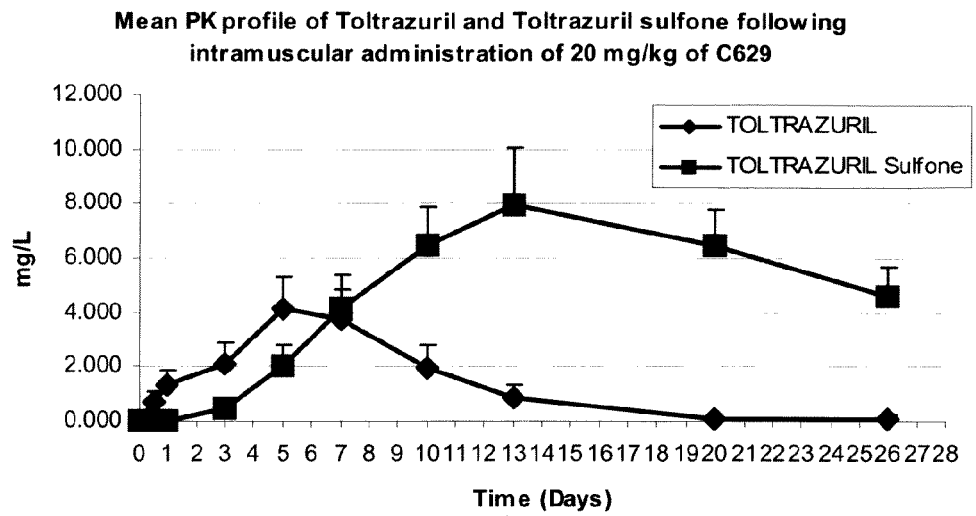
Figure 5:
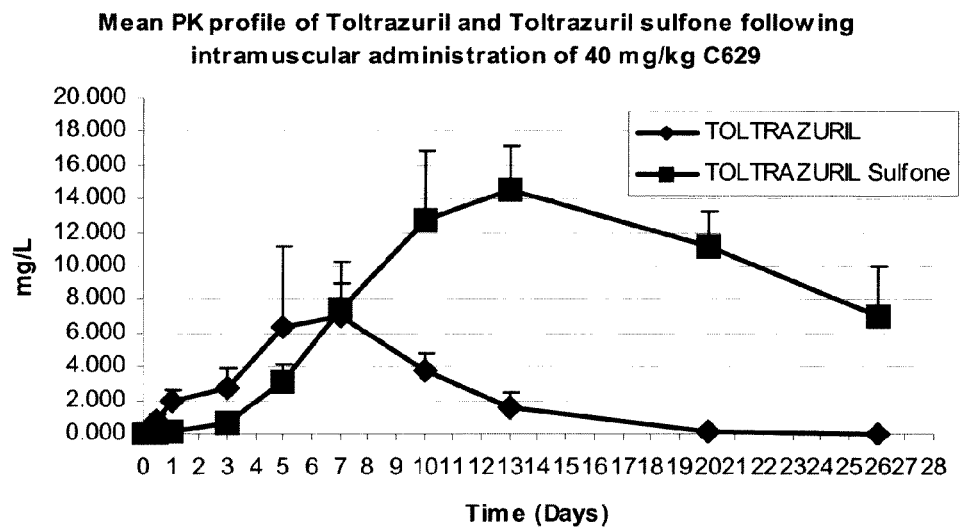
Figure 5:
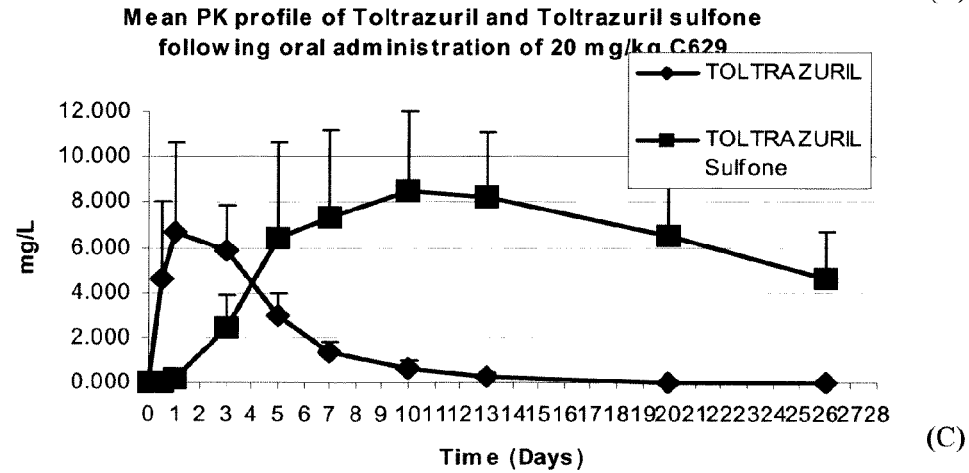

FIG. 5: Mean PK profile of toltrazuril and toltrazuril sulfone following intramuscular injection of 20 mg/kg by body weight (A) or 40 mg/kg by body weight (B) toltrazuril, or following oral administration of 20 mg/kg by body weight toltrazuril (C).

Figure 6:
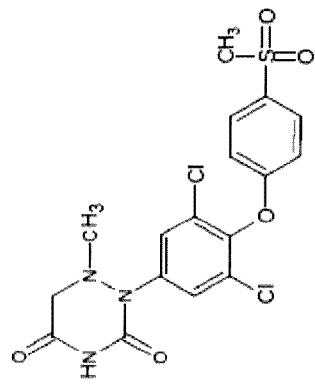
Figure 6:
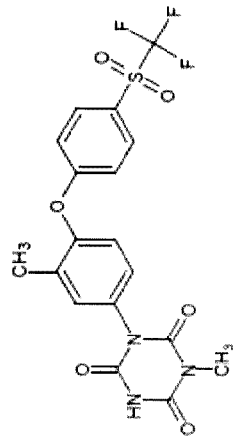
Figure 6:
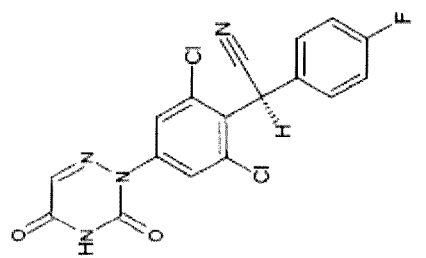
Figure 6:
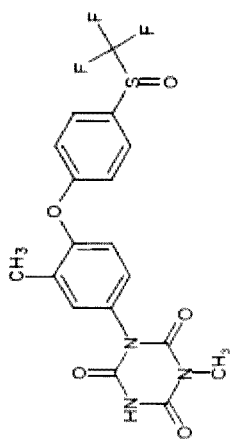
Figure 6:
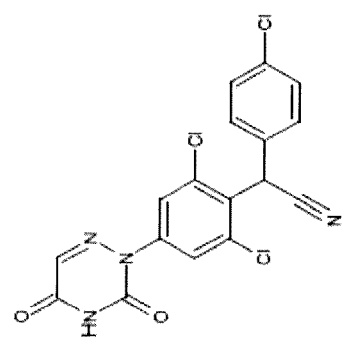
Figure 6:
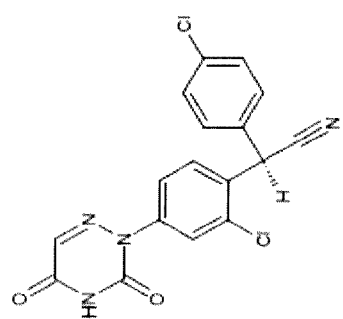
Figure 6:
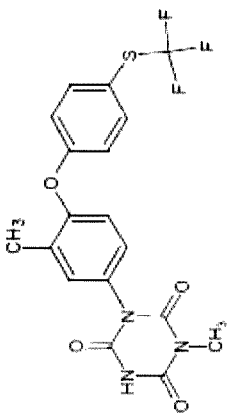

FIG. 6: Structure of triazine compounds.

DETAILED DESCRIPTION OF THE INVENTION

The invention resides in novel compositions and methods for the treatment of non-human animals with triazine compounds. The invention broadly relates to intramuscular or subcutaneous triazines and the uses thereof. The invention, in one aspect, resides in a novel method for administering triazines to non-human animals, either alone or in combination with further active agents. The invention also relates to methods for the preventive treatment of non-human animals using intramuscular or subcutaneous injection of triazines.

Triazine Compounds

The term "triazine(s)" designates a well-known class of active substances, especially against infections with coccidian. Typical triazines for use in a method or composition of the invention are compounds of formula A or B below, of any purity, preferably having a purity of at least 90%, as well as any salt, ester, racemate, isomer, or prodrug thereof:

(formula A)

(formula B)

wherein:
$R^1$ is $R^3$—$SO_2$— or —S—,
$R^2$ is alkyl, alkoxy, halogen or $SO_2N(CH_3)_2$,
$R^3$ is a haloalkyl,
$R^4$ and $R^5$ are independently from each other a hydrogen or Cl atom, and
$R^6$ is fluorine or chlorine.

Triazine compounds include more preferably triazinediones (formula A) and triazinetriones (formula B). Examples of triazinediones include, without limitation, clazuril ($R^4$ is Cl, $R^5$ is H, $R^6$ is Cl in formula A), diclazuril ($R^4$ is Cl, $R^5$ is Cl, $R^6$ is Cl in formula A) or letrazuril ($R^4$ is Cl, $R^5$ is Cl, $R^6$ is F in formula A). Preferred 1,2,4-triazinediones are diclazuril and sulazuril.

Triazines for use in the present invention are, more preferably, triazinetriones of formula B, even more preferably wherein $R^2$ is a C1 to C4 alkyl or alkoxy group (e.g., methyl, ethyl, or n-propyl), and/or $R^3$ is a C1 to C3 perfluoroalkyl group (e.g., trifluoromethyl).

Specific and most preferred triazines of the invention are toltrazuril ($R^1=R^3$—S—, $R^2=CH_3$, $R^3=CF_3$ in formula B) and ponazuril ($R^1=R^3$—$SO_2$—, $R^2=CH_3$, $R^3=CF_3$ in formula B).

Toltrazuril (1-methyl-3-[3-methyl-4-[4-(trifluoromethyl)thio)]phenoxy]phenyl]-1,3,5-triazine(1H,3H,5H)-2,4,6-trione) is widely used in porcine, ovine, bovine and avian for the prevention and treatment of coccidiosis, by oral administration. It is currently available on the market as Cevazuril® or Baycox®. Methods for the preparation of toltrazuril are disclosed in various patents such as U.S. Pat. No. 4,219,552, U.S. Pat. No. 5,219,853, EP 0 201 030, and EP 0 879 057. The chemical structure of toltrazuril is represented in formula (C) below:

(Formula C)

The chemical structures of further examples of triazine compounds for use in the present invention are depicted in FIG. 6.

The triazine(s) as defined is the present invention comprise(s) their salts, such as sodium salts.

Treatment

Within the context of the invention, the term "treatment" includes, particularly, the preventive treatment of non-human animals against a disease. The preventive treatment of a non-human animal against a disease designates a treatment made before the non-human animal has been exposed to or in contact with the causative agent of the disease (e.g., a pathogen, virus, protozoan, cell, etc.), or after said exposure/contact but before development of the symptoms or at an early stage of development of the disease. Also, the term "preventive treatment", in relation to a population of non-human animals, designates the treatment of all members of the population even after the disease has been detected in certain members, to limit or avoid spreading to and contamination of the others.

In a particular embodiment, the term "treatment" designates the protection of a non-human animal against a disease, e.g., against the effect of an exposure to the causative agent, or against the development of the disease in exposed non-human animals. The invention is particularly suited to protect non-human animals against an infectious disease such as a protozoan or microbial disease.

The term "treatment" also includes an increase in the welfare of the treated non-human animals, for example in increasing the production of meat, milk, wool, etc.

The term "treatment" or "preventive treatment" also includes the alleviation of the symptoms, as well as a delay, reduction or cure of an existing infection.

An object of the invention resides in a composition comprising a triazine for use in the preventive treatment of a non-human animal against an infectious disease, wherein said composition is administered by intramuscular or subcutaneous injection.

A particular object of the invention resides in a composition comprising a triazine for use to protect a non-human animal against an infectious disease, wherein said composition is administered by intramuscular or subcutaneous injection.

Another object of the invention resides in a method to protect a non-human animal against an infectious disease, the method comprising the intramuscular or subcutaneous injection of a composition comprising a triazine to said non-human animal.

Another object of the invention resides in a method to protect a non-human mammal against an infectious disease, the method comprising the intramuscular injection of a composition comprising a triazine to said non-human mammal.

Another object of the invention resides in a method to protect an avian against an infectious disease, the method comprising the subcutaneous injection of a composition comprising a triazine to said avian.

Another object of the invention resides in a method for administering a triazine to a non-human animal, the method comprising the intramuscular or subcutaneous injection of a composition comprising said triazine to said non-human animal.

As discussed above, the triazine is preferably a derivative of 1,2,4-triazinedione or a derivative of 1,3,5-triazinetrione, and, more preferably, is toltrazuril.

Intramuscular Injection

An important aspect of the invention resides in the intramuscular administration route. As shown in the experimental section, the invention shows that intramuscular triazine, even after a single administration, provides effective protection in the treated non-human animals, without the need for repeated injections or for long-term or slow-release formulations. Furthermore, the invention shows that intramuscular triazines may be combined with further intramuscular active agents so that an effective treatment is obtained without imposing additional manipulations on the non-human animals.

The compositions of the invention may be administered by intramuscular injection(s) using techniques and/or devices known per se in the art. In this regard, intramuscular injection can be performed with a syringe, a gun, a microneedle injection device, a needle-free injection device, a pulse device, etc. In a preferred embodiment, injection is performed with a needle injector or a syringe. In another particular embodiment, injection is performed with a needle-free injection device such as a pulse needle-free system, more particularly a spring-powered, battery-powered, or compressed-gas-powered device. Specific examples of needle-free technologies are described, e.g., in WO2006/058426, WO2007/140610, and WO2009/111794. A preferred needle-free injection device for use in the present invention is the AcuShot™ needle-free technology described in WO2006/058426 and WO2007/140610.

Intramuscular injection may be made in any muscle. For livestock, such as cattle, intramuscular injection is preferably made in the area of the neck, or behind the ear, rather than in the hind limb/ham muscle or in the inguinal fold. The results presented show that intramuscular triazines exhibit a potent therapeutic effect when administered in the area of the neck. For avian species, administration is preferably performed in muscles adjacent to the breastbone.

In this regard, an object of the invention resides in a composition comprising a triazine for use in the preventive treatment of a non-human animal, wherein said composition is administered by intramuscular injection in the neck or behind the ear for a non-human mammal, and in a muscle adjacent to the breastbone for an avian.

A further object of the invention resides in a composition comprising a triazine for use to protect a non-human animal against an infectious disease, wherein said composition is administered by intramuscular injection in the neck or behind the ear for a non-human mammal, and in a muscle adjacent to the breastbone for an avian.

Another object of the invention resides in a method to protect a non-human animal against an infectious disease, the method comprising the intramuscular injection of a composition comprising an effective amount of a triazine in the neck or behind the ear of said mammal and in a muscle adjacent to the breastbone for an avian.

In an alternative embodiment, especially when the non-human animal is an avian, administration can be performed by subcutaneous injection, e.g., by injection directly below the dermis and epidermis.

In a particular embodiment, the non-human animal has not yet been exposed to the causative agent of the infectious disease and the method can be used to prevent or reduce infection. In another embodiment, the non-human animal has already been exposed to the causative agent and the treatment is used to prevent or delay development of the disease and symptoms, or to reduce or cure the disease, or to avoid/limit disease spreading.

The compositions of the invention are more preferably administered by a single intramuscular or subcutaneous injection to the non-human animal. The results show that a single intramuscular or subcutaneous injection is sufficient to protect a non-human animal against infectious diseases.

In this regard, a preferred embodiment of the invention resides in a composition comprising a triazine for use to protect a non-human animal from an infectious disease, wherein said composition is administered by a single intramuscular injection, preferably in the neck or behind the ear for a non-human mammal and in a muscle adjacent to the breastbone for an avian.

Another object of the invention resides in a method for protecting a non-human animal against an infectious disease, the method comprising a single intramuscular injection, preferably in the neck or behind the ear for a non-human mammal and in a muscle adjacent to the breastbone for an avian, of a composition comprising an effective amount of a triazine for said non-human animal.

Dose

The dose of triazine may vary depending on the non-human animal species and nature of the triazine. Conventional dosage rates from 1 to 60 mg of triazine per kg body weight (mg/kg) of the non-human animal may be used, preferably from 5 to 50 mg/kg, and more preferably from 10 to 30 mg/kg.

Within the context of the invention, the term "effective amount of" designates, preferably, a dose of the active agent which produces a clinical benefit in the treated non-human animals. Particularly, an effective amount is an amount sufficient to reduce infection, disease development, or improve the symptoms.

Preferred dosages for intramuscular toltrazuril are disclosed below, for different non-human mammal species:

pigs: 20 mg/kg body weight/treatment (preferably one single administration);

cattle: 15 mg/kg body weight/treatment (preferably one single administration);

sheep: 20 mg/kg body weight/treatment (preferably one single administration); and poultry: 25 mg/kg body weight/treatment (preferably one single administration).

In this regard, a preferred embodiment of the invention resides in a composition comprising from 1 to 60 mg toltrazuril per kg body weight for use in protecting a non-human animal against an infectious disease, wherein said composition is administered by a single intramuscular or subcutaneous injection, preferably a single intramuscular injection, more preferably in the neck or behind the ear for a non-human mammal and in a muscle adjacent to the breastbone for an avian.

Another object of the invention resides in a method for protecting a non-human animal against an infectious disease, the method comprising a single intramuscular injection, preferably in the neck or behind the ear for a non-human mammal and in a muscle adjacent to the breastbone for an avian, of a composition comprising from 1 to 60 mg toltrazuril per kg bodyweight to said non-human animal.

The compositions may be formulated as a solution or suspension, or any form suitable for intramuscular or subcutaneous injection. The compositions are preferably suspensions. The compositions may further comprise veterinarily acceptable excipient(s) such as solvents, solubilizers, surfactants, antioxidants, thickeners, preservatives, anti-foaming agents, etc. Suitable solvents include, without limitation, physiologically acceptable water, alcohols, esters, vegetable oils and mixtures thereof, in isotonic solutions. Solubilizers include, e.g., polyvinylpyrrolidone. Examples of suitable antioxidants include ascorbic acid, gallic acid esters, and sulfites, and suitable preservatives include, without limitation, benzyl alcohol, n-butanol, benzalkonium chloride, benzoic acid and citric acid. Anti-foaming agents include, without limitation, oil carriers such as mineral oil, vegetable oil, white oil or any other oil that is insoluble in the foaming medium, silicone oil, simethicone emulsion, wax and/or hydrophobic silica such as ethylene bis stear-amide (EBS), paraffinic waxes, ester waxes, silica, fatty alcohol, fatty acid soaps or esters, silicone compound, polyethylene glycol and polypropylene glycol copolymers and alkyl polyacrylates.

An example of a composition for use in the invention is a suspension comprising toltrazuril (between 10 to 30 mg toltrazuril per kg body weight) in water, and an anti-foaming agent.

A specific example of a suspension composition for use in the invention comprises 30 mg of toltrazuril, 3 mg of docusate sodium, 100 mg of polyvinylpyrrolidone, 100 mg of ethanol and water qs for 1 ml.

As indicated above, the composition may comprise further active agents, such as antibiotics, anthelmintics, endectocides, anti-inflammatory agents, vitamins, and/or mineral(s), for single, grouped, separated or sequential intramuscular injection. Preferably, the triazine and the other agent(s) are combined in the same formulation for a single intramuscular or subcutaneous injection.

In a preferred embodiment, the other agent is or comprises iron, preferably an iron complex. Examples of preferred iron complexes include an aqueous colloidal solution of beta-ferric oxyhydroxide and dextran glucoheptonic acid (Gleptoferron commercialized under the trademark Gleptosil® or Ursoferran®); a ferric hydroxide with a low-molecular-weight dextran (commercialized under the trademark Uniferon® or Dexafer®); a ferric hydroxide with macromolecular dextran (commercialized under the trademark Ferroforte®); or a ferric compound of type I.

In a further preferred embodiment, the composition of the invention is a suspension comprising a triazine and an iron complex. More particularly, a specific and preferred example of a composition of the invention is a suspension comprising a triazine, an iron complex, and an anti-foaming agent. A more specific example is a suspension comprising totrazuril (preferably between 10 to 30 mg), an iron complex (preferably a beta-ferric hydroxide), water, and an anti-foaming agent.

In this regard, a further object of the invention resides in a composition comprising a triazine and a further active agent, for protecting a non-human animal against an infectious disease, wherein said composition is administered by intramuscular or subcutaneous injection.

Preferably, both active agents are formulated together, even more preferably as a suspension. In a more preferred embodiment the two active agents are administered as a single intramuscular or subcutaneous injection.

A particular embodiment of the invention resides in a composition for use to protect non-human animals against an infectious disease, wherein the composition comprises a triazine and an iron complex, and wherein the composition is administered by a single intramuscular injection. In a more preferred embodiment, the composition comprises 1 to 60 mg/kg bodyweight triazine and a complex of iron, preferably in suspension.

Infectious Diseases

The invention may be used to treat (e.g., protect, prevent, delay, reduce or cure) an infectious disease in non-human animals, preferably a protozoan or microbial disease. The invention is particularly suited to treat protozoan diseases of the blood and tissues (such as babesiosis, sarcocystosis, or toxoplasmosis), or of the digestive tract (such as coccidiosis).

The invention may be used, in particular, to treat coccidiosis, particularly to prevent or protect non-human animals and more preferably non-human mammals against coccidiosis.

The invention may be used against coccidiosis caused by various protozoans such as *Mastigophora* (*Flagellata*), *Sarcomastigophora* (*Rhizopoda*), *Apicomplexa* (*sporozoa*) *Myxospora, Microspora, pneumocystis carinii* or *ciliophora* (ciliate). Specific examples of *Mastigophora* include Trypanosomatidae such as, without limitation, *Trypanosoma brucei, T. gambiense, T. rhodesiense, T. congolense, T. cruzi, T. evansi*, or *T. equinum*. Specific examples of *Sarcomastigophora* (*Rhizopoda*) include Entamoebidae such as *Entamoeba histolytica* and *Hartmanellidae*, for example *Acanthamoeba* sp. and *Hartmanella* sp. Specific examples of *Apicomplexa* (*Sporozoa*) include Eimeridae, for example *E. acervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium spec., Isospora belli, L. canis, L. felis, L. ohioensis, L. rivolta, L. spec., L. suis, Neospora caninum, N. hugesi, Cystisospora spec., Toxoplasma gondii, Sarcocystis bovicanis, S. bovihominis, Leucozytozoon simondi, Plasmodium berghei, P. falciparum, P. malariae, P. ovate, P. vivax, P. spec., Babesia argentina, B. bovis, B. canis, B. spec., Theileria parva*, and *Theileria spec.*, such as Adeleina, for example *Hepatozoon canis* and *H. spec.* Specific examples of *Myxospora* and *Microspora* include *Glugea spec.* and *Nosema spec.* Specific examples of *pneumocystis carinii* and *Ciliophora* include *Balantidium coli, Ichthiophthirius spec., Trichodina spec.*, and *Epistylis spec.*

Those protozoan genera and species which in pigs lead to subclinical or clinical infections must be very especially emphasized: *Eimeria debliecki, E. suis, E. scabra, E. perminuta, E. spinosa, E. polita, E. porci, E. neodebtiecki, Isospora suis, Cryptosporidium, Toxoplasma gondii, Sarcocystis miescheriana, S. suihominis, Babesia trautmanni, B. perroncitoi*, and *Balantidium coli*.

The invention is effective against all stages of development of the pathogen. Also, the term "protect" includes an increase in the welfare of the infected non-human animal, for example in increasing the production of meat, milk, wool, etc.

The invention may be used in any non-human animals, including porcine, ovine, bovine, canine, feline or avian and preferably livestock, breeding animals, avian animals, companion animals, and laboratory animals. Livestock and breeding animals include mammals such as cattle, horses, sheep, pigs, goats, camels, water buffalos, donkeys, rabbits, fallow deer, reindeer, and fur bearers such as mink, chinchillas and raccoons.

Avian animals include, for example, chickens, hens, ducks, turkeys, guinea fowl, quail, geese, pigeons, parrots, ostriches, and bird species for keeping in domestic premises and in zoos.

Companion animals include, for example, horses, dogs and cats.

Laboratory animals and experimental animals include, for example, mice, rats, guinea pigs, and golden hamsters.

Particular emphasis may be placed on pigs, cattle, sheep and dogs in all species, subspecies and breeds.

The invention is particularly suited for treating pigs, ovines, bovines, horses, sheep, cattle, dogs, rabbits, or cats. It may be used in adults or young non-human animals, such as newborn to 10-day-old non-human animals.

Further aspects and advantages of the invention will be disclosed in the following illustrative Examples section.

EXAMPLES

Example A—Local and General Tolerance of a Single Intramuscular Injection of Toltrazuril in 3-Day-Old Piglets Protocol This target animal safety and efficacy study was conducted on a farm with a known history of cocciodiosis. The main objective was to study the safety and efficacy of intramuscular injection of toltrazuril in comparison to the standard oral application.

Group 1: 8 piglets 3 days old were injected by a single intramuscular dose of toltrazuril (dose=20 mg toltrazuril per kg body weight equivalent to 0.4 mL/kg body weight) on SD0.

Group 2: 8 piglets 3 days old were injected by one intramuscular dose of toltrazuril (60 mg toltrazuril per kg body weight equivalent to 1.2 mL/Kg body weight) on SD0.

Group 3: 8 piglets 3 days old were dosed orally with the standard commercial formulation of toltrazuril, Cevazuril® (dose=20 mg toltrazuril per kg body weight equivalent to 0.4 mL/Kg body weight) on SD0.

Group 4: 12 piglets 3 days old, left untreated.

All four (4) groups of piglets were injected on SD0 with iron (Gleptosil®) at the dose rate of 1 ml per piglet.

Results

The local and general tolerances, as well as body weight development, were assessed. The results are presented in FIG. 1 and FIG. 2 and can be summarized as follows:

Intramuscular doses up to 60 mg/kg were well tolerated.

No pain, limited local reaction (edema) in some piglets injected with 1.2 mL/Kg body weight, disappearing within less than 1 week post injection.

The body weight development was normal in treated piglets.

The intramuscularly treated piglets gained more than control non-treated piglets (+2 kg at SD0+29 days).

Example B—Pharmacokinetics, Safety and Anti-Coccidial Efficacy of Intramuscular Toltrazuril in 2-Day-Old Piglets when Applied Once Protocol Group 1: 10 piglets 2 days old were injected with one intramuscular dose of toltrazuril C629 (dose=20 mg toltrazuril per kg body weight equivalent to 0.4 mL/Kg body weight) on SD0.

Group 2: 11 piglets 2 days old were injected with one intramuscular dose of toltrazuril C629 (dose=40 mg toltrazuril per kg body weight equivalent to 0.8 mL/kg body weight) on SD0.

Group 3: 9 piglets 2 days old were dosed orally with the standard commercial formulation of toltrazuril, Cevazuril® (dose=20 mg toltrazuril per kg body weight equivalent to 0.4 mL/Kg body weight) on SD0.

Group 4: 8 piglets, left untreated.

All four (4) groups of piglets were injected on SD0 with iron injection (Gleptosil®) at the dose rate of 1 ml per piglet. 3 days after treatment (on SD3), the piglets were orally challenged with a characterized strain of *Isospora suis*.

The following study parameters were used to assess the efficacy of the test products:

Local and general tolerance (for Groups 1 and 2);
Occurrence of diarrhea and fecal consistency;
Oocyst excretion;
Body weight development; and
Serum concentrations of toltrazuril and its metabolite toltrazuril sulfone (e.g., ponazuril) in Groups 1, 2 and 3.

Results

The results are presented FIGS. 3 to 5 and in the following Table 1. They can be summarized as follows:

All the tested doses were well tolerated.
No oocyst excretion was observed in treated animals and the fecal consistency was unchanged in treated piglets (G1, G2 and G3).
The animals infected and treated orally or intramuscularly (G1, G2 G3) gained more weight than the control animals (G4).
Toltrazuril is well absorbed after intramuscular application.
The toltrazuril sulfone (e.g., ponazuril) kinetics are not statistically different in animals treated orally (G3) or intramuscularly (G1 and G2).

TABLE 1

| Pharmacokinetic Parameters | Group 1 (i.m. 20 mg/kg) | Group 2 (i.m. 40 mg/kg) |
| --- | --- | --- |
| Tmax (h) | 157 | 171 |
| Cmax (mg/L) | 4025 | 7293 |
| Cmax/Dose | 193 | 182 |
| AUCinf (mg*h/L) | 854714 | 1362678 |
| AUCinf/Dose | 39551 | 34067 |

The invention claimed is:

1. A method for protecting a non-human animal from an infectious disease, comprising administering to said animal in need thereof a composition comprising diclazuril and an iron complex by intramuscular or subcutaneous injection.

2. The method of claim 1, wherein the composition is administered by a single injection to the non-human animal.

3. The method of claim 1, wherein the composition is administered by intramuscular injection in the neck or behind the ear for a non-human mammal, or in a muscle adjacent to the breast-bone for an avian.

4. The method of claim 1, wherein diclazuril is administered between 1 and 60 mg per kg bodyweight or between 10 and 30 mg per kg bodyweight.

5. The method of claim 1, wherein said method further comprising administering one or more additional active agents.

6. The method of claim 5, wherein diclazuril, the iron complex and the additional active agent(s) are combined in the same formulation for a grouped intramuscular or subcutaneous injection.

7. The method of claim 6, wherein diclazuril, the iron complex and the additional active agent(s) are administered in one single injection.

8. The method of claim 1, wherein the composition is a suspension.

9. The method of claim 1, wherein the non-human animal is selected from a porcine, an ovine, a bovine, a canine, a feline, or an avian.

10. The method of claim 1, wherein the method is to protect a non-human animal against a protozoan disease.

11. The method of claim 1, wherein the infectious disease is coccidiosis and the non-human animal is a pig.

12. The method of claim 1, wherein the iron complex is an aqueous colloidal solution of beta-ferric oxyhydroxide and dextran glucoheptonic acid.

13. The method of claim 12, wherein the iron complex is administered to a non-human animal that is a piglet or a calf.

14. The method of claim 5, wherein said one or more additional active agents are selected from antibiotics, anthelmintics, endectocides, anti-inflammatory agents, vitamins, or minerals, for single, grouped, separated or sequential injection with the diclazuril and the iron complex.

15. A method for the protection of a non-human animal against an infectious disease, comprising administering to said non-human animal in need thereof a suspension comprising between 1 and 60 mg of diclazuril and an iron complex by intramuscular injection.

16. The method of claim 15, wherein the iron complex within the suspension is an aqueous colloidal solution of beta-ferric oxyhydroxide and dextran glucoheptonic acid.

17. The method of claim 16, wherein the suspension is administered to a non-human animal that is a piglet or a calf.

* * * * *